(12) United States Patent
Keeling et al.

(10) Patent No.: US 8,359,167 B2
(45) Date of Patent: Jan. 22, 2013

(54) MEASUREMENT OF CARBON CAPTURE EFFICIENCY AND STORED CARBON LEAKAGE

(75) Inventors: Ralph F. Keeling, San Diego, CA (US); Manvendra K. Dubey, Los Alamos, NM (US)

(73) Assignee: Regents of the University of California, Oakland, CA (US)

( * ) Notice: Subject to any disclaimer, the term of this patent is extended or adjusted under 35 U.S.C. 154(b) by 293 days.

(21) Appl. No.: 12/730,031

(22) Filed: Mar. 23, 2010

(65) Prior Publication Data

US 2010/0241363 A1 Sep. 23, 2010

Related U.S. Application Data

(60) Provisional application No. 61/162,602, filed on Mar. 23, 2009.

(51) Int. Cl.
*G01N 31/00* (2006.01)
(52) U.S. Cl. ............... 702/24; 702/22; 702/23
(58) Field of Classification Search ......... 702/22, 702/23.24
See application file for complete search history.

(56) References Cited

U.S. PATENT DOCUMENTS

| | | | | | |
|---|---|---|---|---|---|
| 6,092,430 | A | * | 7/2000 | Liston et al. | 73/863.81 |
| 7,704,746 | B1 | * | 4/2010 | White et al. | 436/56 |
| 2007/0109119 | A1 | * | 5/2007 | Zhang et al. | 340/539.22 |

OTHER PUBLICATIONS

Benson S. et al., "Monitoring protocols and life-cycle costs for geological storage of carbon dioxide", Proceedings of the 7th International Conference on Greenhouse Gas Control Technologies (GHGT-7), Sep. 5-9, 2004, Vancouver Canada (2004).

Bloom, et al.,"Oxygen and carbon dioxide fluxes from barley shoots depend on nitrate assimilation", Plant Physiology, 91, 352-356 (1989).

M. Dubey, et al., "CO2 Measurements to Quantify Potential Leaks from Geosequestration: Technologies for Early Detection", AGU Chapman Conference on the Science and Technology of Carbon Sequestration, Jan. 17-20, 2005, San Diego CA (2005).

Keeling, R.F. et al., "Global and hemispheric COz sinks deduced from changes in atmospheric O2 concentration", Nature, 381, 218-221 (1996).

Lueker, T.J., et al., "The oxygen to carbon dioxide ratios observed in emissions from a wildfire in Northern California", Geophysical Research Letters 28: 2413-2416 (2001).

Moberg, et al., "The IEA Weyburn CO2 monitoring and storage project", Proceedings of the Sixth International Conf. on GHG control (GHGT-6), J. Gale, Y. Kya (EDs), Oct. 1-4, 2002, Kyoto, Japan, 219-224.

Muller, Y. et al., "Trace gas and Particulate Emissions From the 2003 Southern California Wildfires", Los Trans. A GU, 85(47), Fall Meet. Suppl., Abstract A5IC-0792 (2003).

(Continued)

*Primary Examiner* — Janet Suglo

(74) *Attorney, Agent, or Firm* — Mintz, Levin, Cohn, Ferris, Glovsky and Popeo P.C.

(57) ABSTRACT

Data representative of a measured carbon dioxide ($CO_2$) concentration and of a measured oxygen ($O_2$) concentration at a measurement location can be used to determine whether the measured carbon dioxide concentration at the measurement location is elevated relative to a baseline carbon dioxide concentration due to escape of carbon dioxide from a source associated with a carbon capture and storage process. Optionally, the data can be used to quantify a carbon dioxide concentration increase at the first location that is attributable to escape of carbon dioxide from the source and to calculate a rate of escape of carbon dioxide from the source by executing a model of gas-phase transport using at least the first carbon dioxide concentration increase. Related systems, methods, and articles of manufacture are also described.

20 Claims, 4 Drawing Sheets

OTHER PUBLICATIONS

Raines, M, A., et al., "A Review of the Pennsylvanian SACROC Unit", West Texas Geological Society—2001 Fall Symposium (2001).

Seibt, U. et al., "Observations of O2: CO2 exchange ratios during ecosystem gas exchange". Global Biogeochemical Cycles, 18(4) doi:10.1029,20134GB002242 (2004).

Severingliaus, J.P., "Thesis", Columbia University, (1995).

Vest, E. L. Jr., "Oil Fields of Pennsylvanian-Permian Horseshoe Atoll, West Texas", Geology of Giant Petroleum Fields-symposium, aapg, 53d ann. mtg, Oklahoma City, OK, 1968. Memoir-American Association of Petroleum Geologists, p. 185-203 (1970).

* cited by examiner

MEASUREMENT OF CARBON CAPTURE EFFICIENCY AND STORED CARBON LEAKAGE

CROSS-REFERENCE TO RELATED APPLICATIONS

This application claims the benefit of U.S. provisional patent application Ser. No. 61/162,602, filed on Mar. 23, 2009 and entitled "Detection of Carbon Dioxide Leak from Geo-Sequestration with High Precision" which is incorporated by reference herein in its entirety.

GOVERNMENT LICENSE RIGHTS

This invention was made with government support under Award no. DE-AC52-06N025396 awarded by the Department of Energy. The United States government has certain rights in the invention.

TECHNICAL FIELD

The subject matter described herein relates to use of atmospheric signatures of emissions from combustion sources utilizing carbon capture and storage (CCS) and from leakage at CCS storage sites to calculate CCS capture and leakage rates based on atmospheric measurements of one or more of carbon dioxide ($CO_2$) concentration, the oxygen ($O_2$) concentration, and the isotopic distribution of carbon in $CO_2$.

BACKGROUND

A technological option for avoiding the impacts of rising carbon dioxide on the Earth's climate is to capture the carbon dioxide that would otherwise be emitted from stationary industrial sources, such as power plants, and store the $CO_2$ in geological reservoirs, a process known as carbon capture and storage (CCS). A related option is to capture carbon dioxide directly from the atmosphere, a process known as direct air capture (DAC), followed also by storing the $CO_2$ in geological reservoirs.

Effective methods and systems for detecting leakage from geological $CO_2$ sequestration sites as well as quantifying the efficiency of CCS systems can be critical to ensuring that objectives of the sequestration process are being met. Proper accounting of both leakage and capture efficiency is also required under the United Nations Framework Convention on Climate Change. Additionally, the U.S. DOE has specified a target of 0.01% per annum for the maximum leak rate from geologic storage sites. For a large-scale storage site containing 10 to 100 Mton $CO_2$, this corresponds to a $CO_2$ leakage rate of 100 to 1000 tons $CO_2$ per year or 0.032 to 0.32 g $CO_2$ per second. Detection of such tiny leaks above a much larger varying (natural and anthropogenic) background is a technological challenge that is addressed by one or more implementations of the current subject matter.

SUMMARY

In one aspect of the currently disclosed subject matter, a method includes receiving first data representative of a first measured carbon dioxide ($CO_2$) concentration and of a first measured oxygen ($O_2$) concentration at a first measurement location, determining that the measured carbon dioxide concentration at the first measurement location is elevated relative to a baseline carbon dioxide concentration due to escape of carbon dioxide from a source associated with a carbon capture and storage process, and promoting a result indicating possible escape of carbon dioxide from the source.

In optional variations, one or more of the following features can also be included. The determining can include accounting for observed variability in the first measured $CO_2$ concentration expected to be attributable to one or more of respiration or photosynthesis of living organisms, combustion of fossil fuels, combustion of biofuels, or combustion of biomatter in a local vicinity of the first measurement site by detecting a change in a temporal correlation between the first measured $CO_2$ concentration and the first measured oxygen $O_2$ concentration at the first measurement location. The method can also include quantifying, based on the first data, a first carbon dioxide concentration increase at the first location that is attributable to escape of carbon dioxide from the source and calculating a rate of escape of carbon dioxide from the source. The calculating can include executing a model of gas-phase transport using at least the first carbon dioxide concentration increase. The quantifying can optionally include identifying an increase in the measured $CO_2$ concentration that does not occur substantially concurrently with a decrease in the measured oxygen concentration. The source can include a leak from a below-ground storage site for carbon dioxide captured by the carbon capture and storage process or release of carbon dioxide from a fossil fuel combustion installation equipped with a carbon dioxide capture system. Additional data representative of an isotopic ratio of carbon in carbon dioxide at the first measurement site can be received and used in the determining that the measured carbon dioxide concentration at the first measurement location is elevated relative to a baseline carbon dioxide concentration. The first measurement location can be above ground, such that the first data result from analysis of ambient air, or below ground, such that the first data result from analysis of soil gas. The first data can be collected with a sensor system that includes a first analyzer that determines the measured $CO_2$ concentration and a second analyzer that determines the measured $O_2$ concentration.

The first data can be collected with a sensor system that includes a carbon dioxide analyzer that determines the measured carbon dioxide concentration and an oxygen analyzer that determines the measured oxygen concentration. The sensor system can optionally be mobile and can further include a navigation system that determines the first measurement location. Second data representative of a second measured carbon dioxide concentration and of a second measured oxygen concentration at a second measurement location can be used with at least the first data to isolate a source location for the source.

Articles are also described that comprise a tangibly embodied machine-readable medium operable to cause one or more machines (e.g., computers, etc.) to result in operations described herein. Similarly, computer systems are also described that may include a processor and a memory coupled to the processor. The memory may include one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

As noted, carbon capture and storage (CCS) can affect atmospheric composition by reducing the $CO_2$ released from fossil-fuel burning without reducing the associated $O_2$ loss due to consumption of oxygen by the combustion process. $CO_2$ that leaks into the air from below-ground CCS sites also distinctively lacks an $O_2$ deficit that would normally be associated with carbon dioxide production by soil respiration. As described in greater detail below, aspects of the current subject matter use measurements of $CO_2$ concentrations, $O_2$ concentration, and optionally one or more of the $^{13}C/^{12}C$ and $^{14}C/^{12}C$ ratios of $CO_2$ to detect and/or quantify leakage from a below ground storage installation as well as to gauge the carbon capture efficiency of a combustion or other source utilizing CCS.

This method relies on the novel use of simultaneous measurements of carbon dioxide and oxygen concentrations at high precision to improve the ability to detect leakage of captured $CO_2$ and optionally also to improve the ability to isolate sources and quantify leakage rates of $CO_2$. The method applies to measurement of concentrations in the free atmosphere, in soil gas, or in aqueous media, such as ground waters, lakes, or seawater.

Detecting leakage of captured $CO_2$ into the environment can be difficult because the variations in $CO_2$ concentration caused by the leakage are small and hard to distinguish from much larger variations in $CO_2$ concentration caused by other natural processes and energy related emissions. Important causes of additional variability typically include photosynthesis or respiration of living organisms such as soil microbes or vegetation or combustion of fossil fuels or biofuels.

Photosynthesis consumes $CO_2$ and proportionally releases $O_2$, while respiration and combustion processes release $CO_2$ and proportionally consume $O_2$. In contrast, leakage of sequestered $CO_2$ is not associated with either consumption or production of $O_2$. A change in $CO_2$ concentration which occurs in the absence of a change in $O_2$ concentration can therefore be used as a sensitive fingerprint of leakage. These principles apply both in the air, in soil gas, or in aqueous media. In the atmosphere, changes in $O_2$ concentration are typically reported in terms of the impact on the $O_2/N_2$ ratio. In aqueous media, the "$CO_2$ concentration", as relevant for leak detection and quantification, can be determined from measurements of salinity and temperature plus two or more of the following: $CO_2$ fugacity, the pH, the total inorganic carbon concentration.

Figure 1:
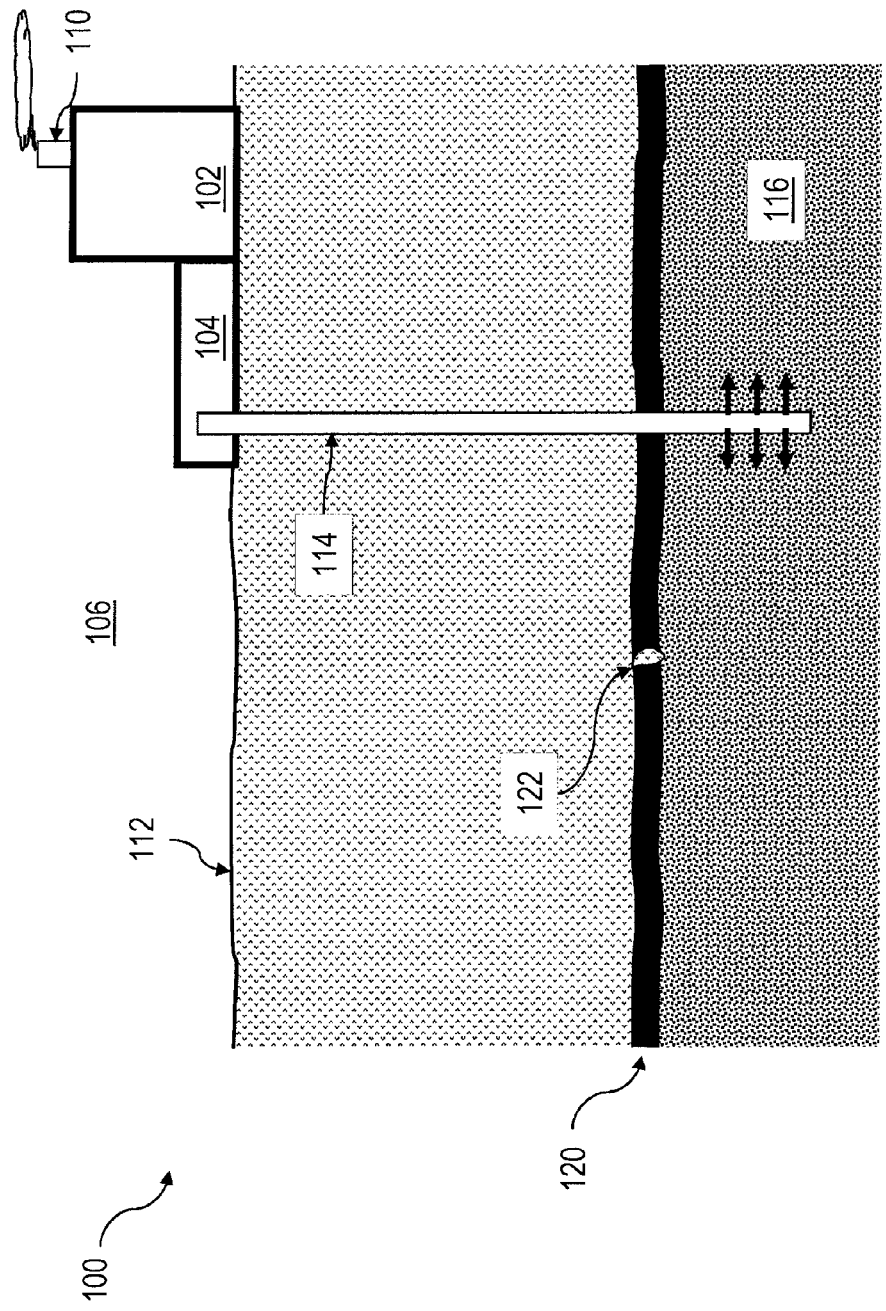
FIG. 1 shows a schematic diagram illustrating elements of an example of a carbon capture and storage system.

FIG. 1 shows a schematic diagram 100 illustrating a representative carbon capture and storage arrangement and budget. Other configurations and sizes or scales of such systems are within the scope of this disclosure and likewise amendable to use with the inventive subject matter disclosed herein. As shown in FIG. 1, a source 102 of carbon dioxide emissions can include a carbon capture system 104 that captures and diverts some or all of the $CO_2$ produced by the source 102 from being emitted into the atmosphere 106 via a stack or other exhaust system 110 at the source 102. The source 102 can in some examples be a large stationary $CO_2$ source, such as for example, a power plant, a cement plant, a factory, or the like. The captured $CO_2$ can be compressed and pumped below the ground surface 112, for example via an injection well 114 that delivers the compressed $CO_2$ to a permanent or quasi-permanent geologic reservoir 116, such as for example, a saline aquifer, depleted oil reservoir, below the sea floor, etc. Capture of $CO_2$ directly from the atmosphere 106 may also be possible using a process known as direct air capture (DAC), which has the potential of reducing atmospheric $CO_2$ to below current levels if implemented at large enough scales.

Referring again to FIG. 1, the $CO_2$ pumped below ground as part of a CCS or DAC process or by a CCS system 104 generally exists as a buoyant supercritical fluid that can tend to migrate toward the ground surface 112 unless contained beneath a continuous cap rock 120. Even where the cap rock 120 appears continuous, however, leakage may occur via one or more mechanisms that can include, but are not limited to, leakage through an improperly sealed injection well 114 or other pre-existing well, permeation through the cap rock 120, and leakage through one or more faults 122 in the cap rock 120. A well leak can create a point-source at the well 114 while permeation can create a wide-spread area source and leaks through faults 122 can create line sources or hot spots.

Seismic or electromagnetic methods can be used to track $CO_2$ flow below ground, and soil sampling may help detect $CO_2$ plumes near the ground surface 112. However, these techniques may not be sufficient to quantify leakage accurately or to rule out leakage through faults or wells 112, in particular. Tracers, such as for example sulfur hexafluoride ($SF_6$) can be injected along with the captured $CO_2$. Monitoring of the tracer gas concentrations can be used to estimate leakage rates from the stored carbon reservoir. Use of tracers can be hindered by the cost and effort of injecting the tracer with the captured $CO_2$, given the large scale of the activity. Furthermore, many of these tracers, such as for example $SF_6$ and perfluoro carbons, are themselves very powerful greenhouse gases. Additionally, the tracer may not behave as in the same manner, either physically or chemically, as $CO_2$. Other methods to detect and/or quantify $CO_2$ leakage from underground storage or problems with the efficiency of a CCS system have included using some fingerprint or other characteristic of the emitted $CO_2$, for example the isotopic ratios (of $^{12}C$, $^{13}C$, and $^{14}C$). As discussed in more detail below, for several reasons these methods may also not be amenable to accurate and reproducible identification and/or quantification of carbon emissions associated with CCS in many situations.

The effect of CCS on atmospheric composition both locally, regionally, and globally is more complex than its impacts on the rate at which $CO_2$ is added to the atmosphere. While a CCS system can reduce the $CO_2$ emissions from a source 102 that produces $CO_2$ through combustion of fossil fuels or biomass, such a system does not reverse the $O_2$ loss and the associated impact on the $O_2$ concentration ratio resulting from the combustion process. Thus, the exhaust plume of a combustion-based $CO_2$ source equipped with a CCS system 104 contains an $O_2$ deficit comparable to such a source 102 without CCS, but without the accompanying excess of $CO_2$ that would occur in the absence of CCS. Thus, CCS can reduce the spatial gradients and short-term variability in $CO_2$ concentrations attributable to combustion sources while leaving the spatial gradients and short-term variability in $O_2$ concentration unaffected. The atmosphere near the ground will typically exhibit variations in $CO_2$ and $O_2$ concentration driven by photosynthesis and respiration of local vegetation as well as other local sources and variation in the background atmosphere. $CO_2$ exchange with vegetation and soils typically drives a diurnal cycle in $CO_2$ concentrations near the ground, driven by the day-night cycle of net photosynthesis/respiration and the day-night cycle in vertical mixing. In a stable nocturnal boundary layer, $CO_2$ concentrations often rise above the free-tropospheric background by tens to hundreds of ppm, while day-time values typically drop below free tropospheric values only by a few ppm. Field studies show that the near-surface $CO_2$ variations are typically strongly correlated with variations in $^{13}C/^{12}C$ ratio of the $CO_2$ and the $O_2$ concentration. (Lueker, T. J., R. F. Keeling and M. K. Dubey, 2001: The oxygen to carbon dioxide ratios observed in emissions from a wildfire in Northern California. Geophysical Research Letters, 28, 2413-2416.) (Bowling, D. R., S. P. Burns, T. J. Conway, R. K. Monson and J. W. C. White, 2005: Extensive observations of CO2 carbon isotope content in and above a high-elevation subalpine forest. Global Biogeochemical Cycles, 19.) The correlations can depend, for example in the case of $^{13}C/^{12}C$ on the average isotopic composition of the $CO_2$ that is added or removed by vegetation and in the case of $O_2$ concentration, on the oxidative state of the organic matter that is being created or destroyed as well as the cycling of nitrogen.

Figure 2:
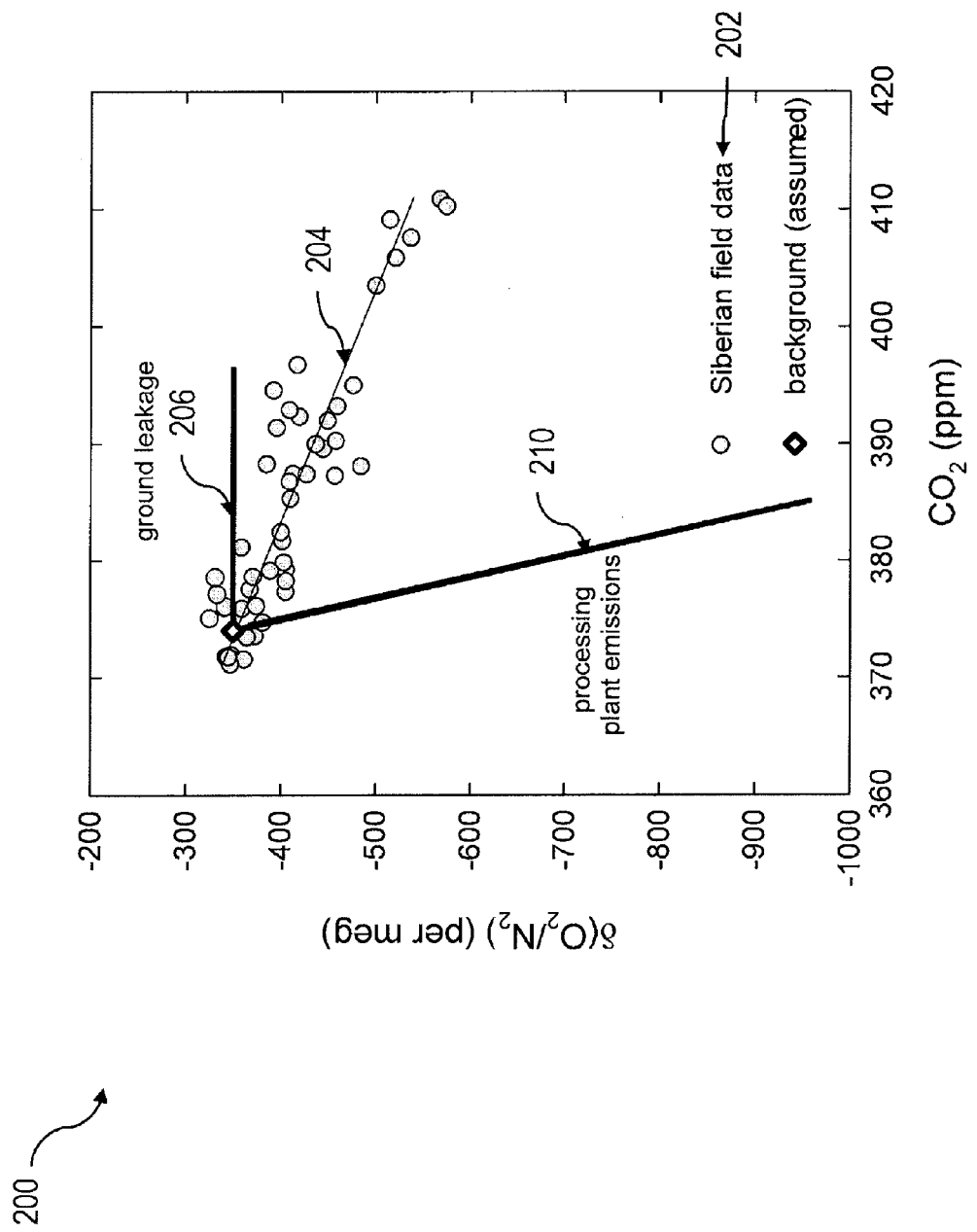
FIG. 2 shows a scatter plot illustrating changes in atmospheric $O_2/N_2$ ratio versus $CO_2$ mole fraction measured with roughly 20-minute resolution at a height of 4 m in the boreal forest of central Siberia.

The ability to use $O_2$ measurements to distinguish different sources of $CO_2$ in proximity to a carbon capture and storage site are illustrated in FIG. 2, which shows a scatter plot of $O_2$ concentration (reported as the $O_2/N_2$ ratio) and $CO_2$ concentration from a site in Siberia (as reported by Kozlova, E. A., A. C. Manning, Y. Kisilyakhov, T. Seifert and M. Heimann, 2008: Seasonal, synoptic, and diurnal-scale variability of biogeochemical trace gases and $O_2$ from a 300 m tall tower in central Siberia. Global Biogeochemical Cycles, 22.). Superimposed on this plot are additional variations that might be expected in proximity to a carbon capture and storage site due $CO_2$ leakage from below ground storage and $CO_2$ releases and $O_2$ consumption from a processing plant. This juxtaposition of synthetic data is provided to illustrate the main features to be expected downwind of a generic sequestration site, while allowing also for variability from vegetation and background atmosphere. The Siberian data 202 tend to fall along a line 204 having a slope of around 5.03 per meg per ppm, which corresponds to a molar $O_2/C$ exchange ratio of 1.05. Day-time data appear mostly in the upper left of FIG. 2 at higher $CO_2$ concentrations while night-time data are spread across the rest of the plot. Such behavior is nearly universal within land ecosystems, reflecting the close relationship between $CO_2$ and $O_2$ exchanges driven by land photosynthesis and respiration. Urban areas can have different ratios reflecting fossil-fuel combustion. However, even in urban settings, tight correlations can be observed (Keeling, R. F., 1988: Measuring correlations between atmospheric oxygen and carbon-dioxide mole fractions—a preliminary-study in urban air. Journal of Atmospheric Chemistry, 7, 153-176).

The synthetic data for the $CO_2$ sources from the leak 206 and the processing plant 210 have characteristic slopes on the $O_2:CO_2$ plot in FIG. 2 that are both different from each other as well as different from that of the ecosystem. The $CO_2$ source from leakage increases $CO_2$ concentrations without changing the $O_2/N_2$ ratios, leading to variations that plot along a horizontal line on the scatter plot.

The processing plant plume lies along a line on a plot of $O_2/N_2$ vs. $CO_2$ having a slope, when expressed in molar ($O_2$:C) units, equal to $r_f/(1-e)$ where $r_f$ is the $O_2$:C combustion ratio of the fuel and e is the processing plant capture efficiency. The combustion ratio $r_f$ of fossil-fuels can be directly determined from their elemental composition. In fact this ratio is used by Leuker et al. to discriminate fire sources with different combustion ratios $r_f$ (Lueker, T. J., R. F. Keeling and M. K. Dubey, 2001: The oxygen to carbon dioxide ratios observed in emissions from a wildfire in Northern California. Geophysical Research Letters, 28, 2413-2416.) In FIG. 2, the processing plant is assumed to be burning coal with a $O_2$:C combustion ratio of 1.15 and to achieve 90% capture efficiency (e=0.9) leading to slope equivalent to an $O_2$:C ratio of 11.5. Combining elemental composition data with atmospheric measurements thus provides an approach that can remotely measure capture efficiency, e. This approach may prove more accurate than assessments based on stack emissions, although certain complications would also need to be addressed. One such complication is that the $O_2$ losses and $CO_2$ releases from a capture plant may not always be perfectly collocated in space and time, leading to several distinct plumes from the plant itself, one depleted in $O_2$ and the other enriched in $CO_2$.

The ability to detect leakage as a deviation from the expected trend on the $O_2/N_2:CO_2$ plot, as in FIG. 2, depends on the scatter in the linear relationship, which has contributions from both measurement imprecision and atmospheric variability. Ultimate sensitivities to leakage $CO_2$ of order 1 to 2 ppm or even better should be feasible, which would be sufficient for detecting point sources of order 1000 ton C $yr^{-1}$ at distances of order 1 km under modest wind conditions, as suggested in the Leuning et al. study (described above). A source detected in this way can be quantified by tracking down its location and making measurements in closer proximity, where $CO_2$ signals of order 10 to 100 ppm might be realized.

The ability to distinguish leakage $CO_2$ from other sources opens the possibility of detecting plumes with even greater sensitivity under light wind conditions. The $CO_2$ from leaks can build up to much higher levels under such conditions, thereby causing larger deviations from the natural $O_2/N_2:CO_2$ relationship. A measurement system in the vicinity of a sequestration site can be used according to implementations of the current subject matter for detecting leaks over a fairly wide area. Under light wind conditions, areal leaks of order 1000 Ton C $yr^{-1}$ or smaller can be detected despite such areal leaks tending to produce $CO_2$ concentration signals that can be an order of magnitude or more smaller than point sources under modest wind conditions. Accurate characterization of the natural $O_2$:C ratio of the ecosystem or other local sources will aid in leak detection and quantification. In one example, multiple measurements systems can be installed over the landscape in the vicinity of such an areal source, with one or more of the multiple measurements systems used as controls.

A method of detecting leakage using combined measurements of $CO_2$ concentration and the $^{13}C/^{12}C$ ratio of $CO_2$ has been previously proposed (e.g. Leuning et al.). For $^{13}C/^{12}C$ data to be useful for leak detection, the exogenous $CO_2$ from CCS must have a distinctly different isotopic composition from $CO_2$ of other nearby sources. However, the isotopic composition of most coals and petroleum has been found to occur in the range of about −24 to −30%, which is similar to the range for $CO_2$ released and taken up by respiration, photosynthesis. $^{13}C/^{12}C$ measurements will therefore not generally provide a clear fingerprint of $CO_2$ released from such fuels. Isotopic measurement can be more useful in identifying impacts of CCS efficiency and/or leakage for $CO_2$ generated from processes other than coal. For example, thermogenic $CO_2$, which can occur as a contaminant in natural gas, can have $\delta^{13}C$ as high as −6%, which might be easily distinguished. A thermogenic plume characterized by a $CO_2$ concentration difference on the order of 4 to 5 ppm would be readily distinguishable from the natural variability. $CO_2$ from natural gas, which can have a $\delta^{13}C$ as low as −45%, might also be readily detectable. Isotopic measurements may also be more useful in identifying CCS impacts if the local ecosystem is dominated by C4 grasses, which typically have a characteristic $\delta^{13}C$ on the order of −13%. Combined measurements of $O_2/N_2$ and $CO_2$ concentration may prove more universally applicable for leak detection.

A method of detecting leakage using combined measurements of $CO_2$ concentration and the radiocarbon ($^{14}C$) content of $CO_2$ has also been proposed. $CO_2$ derived from fossil-fuel burning is devoid in radiocarbon. In contrast, $CO_2$ in the atmosphere, as well as $CO_2$ from respiration or combustion of biomass or biofuels, or contains measureable amounts of radiocarbon. These differences can be exploited to aid in leak detection. The application of radiocarbon measurements to detect leakage suffers from the limitation, however, that the radiocarbon cannot currently be measured directly in the field, requiring both field sampling and transport of samples to an analytical facility, which increases costs limits sampling coverage, and imposes time delays. Various implementations of the current subject matter enable verification of rates of CCS via changes in the atmosphere, both in the near field, for example within a few kilometers of processing plants and storage sites. Atmospheric detection of CCS (and leakage) is possible using differences in the exchange ratios ($O_2:C^{13}C/^{12}C$, and $^{14}C/^{12}C$) of CCS relative to other processes, as summarized in Table 1. In the near field, for example, combined measurements of $CO_2$ concentration with measurements of $O_2$ concentration and/or $\delta^{13}C$ can help to resolve the signatures of leakage or incomplete capture in the face of variability due to vegetation and soils.

TABLE 1

Nominal exchange ratios for $CO^2$ source/sink processes

|  | $\delta(O_2/N_2):CO_2$ per meg/ppm | $\delta^{13}C:CO_2$ per mil/ppm[1] | $\Delta^{14}C:CO_2$ per mil/ppm |
|---|---|---|---|
| Fossil-fuel burning | −6.7 | −0.045 | −2.5 |
| Land biospheric sink | −5.2 | −0.048 | 0 |
| Ocean sink | 0 | −0.005 | 0 |
| Isoflux | not applicable | ∞ | ∞ |
| Carbon capture & storage | 0 | −0.045 | −2.5 |
| Direct air capture | 0 | −0.013 | 0 |

[1]Estimates based on a $CO_2$ concentration of 400 ppm, and fractiona,ion $^o f^{-1}$8‰ and $^{-5‰}$$^{fo}$r the land sink and direct air capture, respectively.

In the near field, detecting the $CO_2$ excess from leakage is only the first step. Also important are interpretations of observed concentration changes in terms of fluxes, which requires some form of inverse or forward modeling. This is an active field, and much progress can be expected in the near future. Leauning et al. (cited above) describes an approach to such modeling that requires as inputs for this analysis identifications of $CO_2$ concentrations at one or more monitoring sites that are attributable to a given source. These values can be obtained using the current subject matter as discussed herein. Better definition of $O_2:CO_2$ and $\delta^{13}C$ exchange ratios of local ecosystems and their variability can also be helpful. Field measurement programs can be performed using instrumentation placed in proximity to potential leakage sites and in nearby locations as controls. Based on present understanding of land ecosystem exchange ratios and available measurement technology, leakage of $CO_2$ can be detected to the levels of ~2 ppm or better under a wide range of circumstances, even with active vegetation. In sites with less active vegetation, such as arid regions where many favorable geosequestration sites exist, even lower detection limits are feasible. The ability to discriminate between leakage and ecosystem $CO_2$ exchanges makes it possible to resolve emissions under near stagnant conditions, when $CO_2$ excesses will build to high levels. This ability is important for leak detection and addressing issues of public safety.

Other process besides land ecosystem exchange can produce atmospheric signatures that may interfere with the signatures of CCS in near-field applications. Fossil-fuel burning can occur in varying $O_2:C$ ratios, depending on fuel type, and this may cause variability in many settings, particularly in urban or industrial settings. Cement manufacture, which releases $CO_2$ without the normal $O_2$ deficit (produced via thermal decomposition of limestone) may interfere in some settings. Increased use of hydrogen gas ($H_2$) gas as an energy carrier, e.g. derived ultimately from fossil-fuels, will alter patterns of $CO_2$ production and $O_2$ consumption from fossil-fuels by separating the point of $CO_2$ production (associated with $H_2$ production) from the $O_2$ consumption (associated with energy end use). Such complications may prove problematic in some cases.

Figure 3:
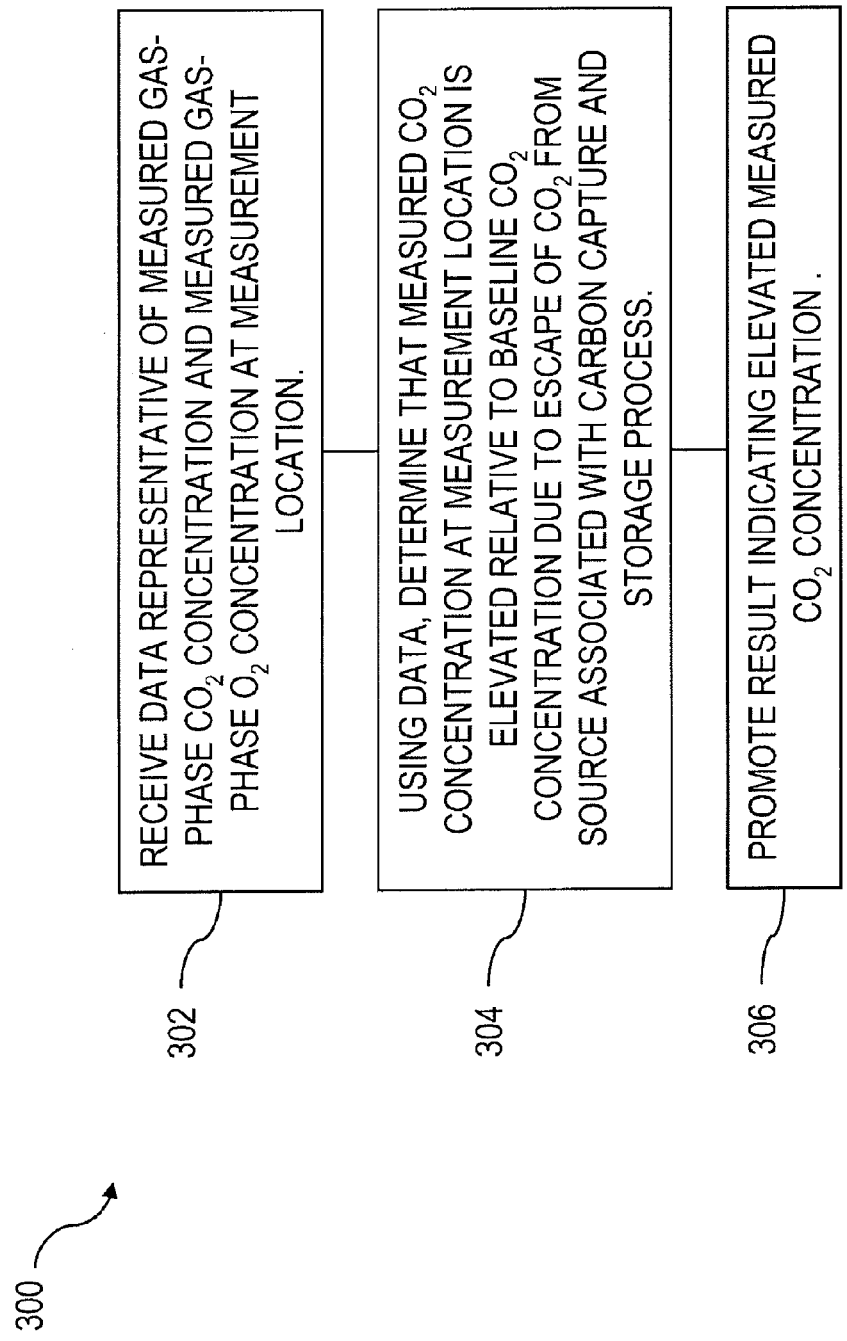
FIG. 3 shows a process flow chart illustrating a method in accordance with one or more implementations of the current subject matter.

FIG. 3 shows a process flow chart 300 that illustrates a method according to an implementation of the current subject matter. At 302, a processor receives data representative of a measured $CO_2$ concentration and of a measured $O_2$ concentration at a measurement location. The measurement location can optionally be above ground, for example if the data result from analysis of ambient air, or below ground, for example if the data result from analysis of soil gas, or in aqueous media, for example if the data result from analysis of ground water, seawater, or sediment pore-water. At 304, the processor determines, using input data comprising the data, that the measured carbon dioxide concentration at the first measurement location is elevated relative to a baseline carbon dioxide concentration due to escape of carbon dioxide from a source associated with a carbon capture and storage process. The baseline carbon dioxide concentration is what would be present absent effects of leakage of stored carbon dioxide or inefficient capture of a CCS process or system. At 306, a result is promoted indicating the elevated measured $CO_2$ concentration. The promoting can optionally include one or more of generating or displaying a message on a monitor or printout, sending a message regarding the result, storing a data flag indicative of the elevated measured $CO_2$ concentration, or the like.

The determining can include accounting for observed variability in the first measured $CO_2$ concentration expected to be attributable to photosynthesis, respiration, or other activities of living organisms, or combustion biofuels or fossil-fuels in a local vicinity of the first measurement site. This accounting can be accomplished by detecting a change in a temporal correlation between the first measured oxide $CO_2$ concentration and the first measured $O_2$ concentration at the first measurement location. As noted above, $CO_2$ escaping from a carbon capture and storage process or site tends to increase the $CO_2$ concentration observed at a measurement location without an accompanying deficit in the $O_2$ concentration. For example, an increase in the measured $CO_2$ concentration that does not occur substantially concurrently with a decrease in the measured $O_2$ concentration can indicate that the $CO_2$ concentration increase is due to escape of $CO_2$ from a CCS storage site or CCS system or process. The source can include a leak from a below-ground storage site for carbon dioxide captured by the carbon capture, transport, and storage process. Alternatively, the source can include release of $CO_2$ from a fossil fuel combustion installation equipped with a carbon dioxide capture system. As noted above, the $CO_2$ released from a fossil-fuel combustion installation or alternately from a biofuel combustion is associated with an unusually large reduction in $O_2$.

Figure 4:
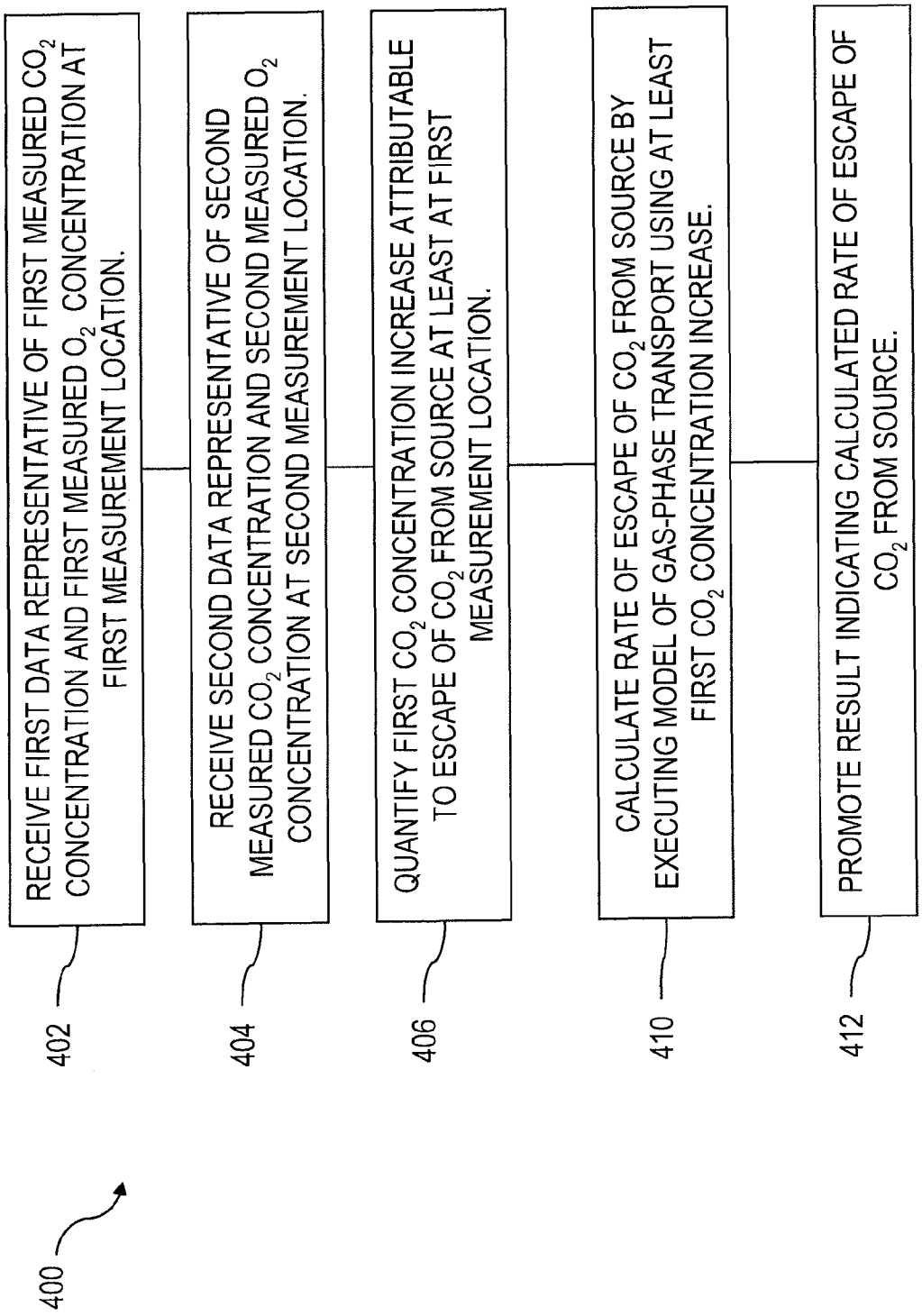
FIG. 4 shows a process flow chart illustrating a second method in accordance with one or more implementations of the current subject matter.

FIG. 4 shows a process flow chart 400 that illustrates a method according to a further implementation of the current subject matter. At 402, the processor receives first data data. The first data are representative of a first measured $CO_2$ concentration and of a first measured $O_2$ concentration at a first measurement location. Optionally, at 404, the processor can receive second data that are representative of a second measured $CO_2$ concentration and of a second measured $O_2$ concentration ratio at a second measurement location. The second measurement location can be closer or more distant from the source than the first measurement location. At 406, the processor quantifies a first carbon dioxide concentration increase at the first location that is attributable to escape of carbon dioxide from the source and a second carbon dioxide concentration increase at the second location that is attributable to escape of carbon dioxide from the source. The quantifying can include identifying an amount of the carbon dioxide in the first carbon dioxide concentration, or alternatively in the first and the second measured carbon dioxide concentrations, that is not correlated with a comparable deficit in the $O_2$ concentration at the first measurement location, or alternatively in the first and the second measurement locations. At 410 a rate of escape of carbon dioxide from the source is calculated by executing a model of gas-phase transport whose input data includes the first carbon dioxide concentration increase, or alternatively the first and the second carbon dioxide concentration increase. Other inputs to such a model can include weather data such as wind and temperature. An example of such a model is described in the paper by Leuning et al. cited above. At 412, a result is promoted indicating the calculated rate of escape of carbon dioxide from the source. Furthermore, measurement systems according to implementations of the current subject matter can be also mobile and can follow changes in measured $CO_2:O_2$. Coupling of measurements collected as described herein with atmospheric transport models can also facilitate tracking and even isolation of leakage areas. This isolation can allow the leakage to be fixed and, if necessary, appropriate evacuation plans be implemented to avoid human or other casualties (e.g. Lake Nyos disaster).

Additional data representative of an isotopic ratio, for example $^{14}C/^{12}C$ and/or $^{13}C/^{12}C$, of carbon in carbon dioxide at a measurement site can also be used in the attribution of an elevation in measured $CO_2$ concentration. Such measurements can be performed using one or more methods, including but not limited to infrared spectroscopy for $CO_2$ concentrations; gas chromatography with thermal conductivity detection, paramagnetic techniques, vacuum-ultraviolet absorption (for example at a wavelength of about 147 nm), and fuel-cell analysis for the $O_2$ concentration; tunable diode laser system for $\delta^{13}C$; and mass spectrometry for $^{14}C/^{12}C$ The subject matter described herein can be embodied in systems, apparatus, methods, and/or articles depending on the desired configuration. In particular, various implementations of the subject matter described herein can be realized in digital electronic circuitry, integrated circuitry, specially designed application specific integrated circuits (ASICs), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input.

The subject matter described herein can be implemented in a computing system that includes a back-end component, such as for example a data server, or that includes a middleware component, such as for example an application server, or that includes a front-end component, such as for example a client computer having a graphical user interface or a Web browser through which a user can interact with an implementation of the subject matter described herein, or any combination of such back-end, middleware, or front-end components. The components of the system can be interconnected by any form or medium of digital data communication, such as for example a communication network. Examples of communication networks include, but are not limited to, a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow depicted in the accompanying figures and/or described herein do not necessarily require the particular order shown, or sequential order, to achieve desirable results. Other implementations may be within the scope of the following claims.

What is claimed:

1. A method comprising:
receiving, at a processor, first data representative of a first measured carbon dioxide ($CO_2$) concentration and of a first measured oxygen ($O_2$) concentration at a first measurement location;
determining, by the processor using input data comprising the first data, that the measured carbon dioxide concentration at the first measurement location is elevated relative to a baseline carbon dioxide concentration due to escape of carbon dioxide from a source associated with a carbon capture and storage process, the determining comprising accounting for observed variability in the first measured carbon dioxide concentration expected to be attributable to one or more of respiration or photosynthesis of living organisms, combustion of fossil fuels, combustion of biofuels, or combustion of biomatter in a local vicinity of the first measurement site, the accounting for comprising detecting a change in a temporal correlation between the first measured carbon dioxide concentration and the first measured ox :en concentration at the first measurement location; and
promoting a result indicating possible escape of carbon dioxide from the source.

2. A method as in claim 1, wherein the first measurement location is above ground, such that the first data result from analysis of ambient air, or below ground, such that the first data result from analysis of soil gas.

3. A method as in claim 1, further comprising:
collecting the first data with a sensor system that comprises a carbon dioxide analyzer that determines the measured carbon dioxide concentration and an oxygen analyzer that determines the measured oxygen concentration.

4. A method as in claim 3, wherein the sensor system is mobile and further comprises a navigation system that determines the first measurement location.

5. A method comprising:
receiving, at a processor, first data representative of a first measured carbon dioxide ($CO_2$) concentration and of a first measured oxygen ($O_2$) concentration at a first measurement location;
determining, by the processor using input data comprising the first data, that the measured carbon dioxide concentration at the first measurement location is elevated relative to a baseline carbon dioxide concentration due to escape of carbon dioxide from a source associated with a carbon capture and storage process;
quantifying, based on the first data, a first carbon dioxide concentration increase at the first location that is attributable to escape of carbon dioxide from the source;
calculating a rate of escape of carbon dioxide from the source, the calculating comprising executing a model of transport using at least the first carbon dioxide concentration increase; and
promoting a result indicating possible escape of carbon dioxide from the source.

6. A method as in claim 5, wherein the quantifying comprises identifying an increase in the measured carbon dioxide concentration that does not occur substantially concurrently with a decrease in the measured oxygen concentration.

7. A method as in claim 5, further comprising:
collecting the first data with a sensor system that comprises a carbon dioxide analyzer that determines the measured carbon dioxide concentration and an oxygen analyzer that determines the measured oxygen concentration.

8. A method comprising:
receiving, at a processor, first data representative of a first measured carbon dioxide ($CO_2$) concentration and of a first measured oxygen ($O_2$) concentration at a first measurement location;
determining, by the processor using input data comprising the first data, that the measured carbon dioxide concentration at the first measurement location is elevated relative to a baseline carbon dioxide concentration due to escape of carbon dioxide from a source associated with a carbon capture and storage process, the source comprising at last one of a leak from a below-ground storage site for carbon dioxide captured by the carbon capture and storage process and a release of carbon dioxide from a fossil fuel combustion installation equipped with a carbon dioxide capture system; and
promoting a result indicating possible escape of carbon dioxide from the source.

9. A method as in claim 8, further comprising:
collecting the first data with a sensor system that comprises a carbon dioxide analyzer that determines the measured carbon dioxide concentration and an oxygen analyzer that determines the measured oxygen concentration.

10. A method comprising:
receiving, at a processor, first data representative of a first measured carbon dioxide ($CO_2$) concentration and of a first measured oxygen ($O_2$) concentration at a first measurement location and additional data representative of an isotopic ratio of carbon in carbon dioxide at the first measurement site;
determining, by the processor, that the measured carbon dioxide concentration at the first measurement location is elevated relative to a baseline carbon dioxide concentration due to escape of carbon dioxide from a source associated with a carbon capture and storage process, the determining comprising using the first data and the additional data; and
promoting a result indicating possible escape of carbon dioxide from the source.

11. A method as in claim 10, further comprising:
collecting the first data with a sensor system that comprises a carbon dioxide analyzer that determines the measured carbon dioxide concentration and an oxygen analyzer that determines the measured oxygen concentration.

12. A method comprising:
receiving, at a processor, first data representative of a first measured carbon dioxide ($CO_2$) concentration and of a first measured oxygen ($O_2$) concentration at a first measurement location and second data representative of a second measured carbon dioxide concentration and of a second measured oxygen concentration at a second measurement location;
determining, by the processor using input data comprising the first data, that the measured carbon dioxide concentration at the first measurement location is elevated relative to a baseline carbon dioxide concentration due to escape of carbon dioxide from a source associated with a carbon capture and storage process;
isolating a source location for the source using at least the first data and the second data and
promoting a result indicating possible escape of carbon dioxide from the source.

13. A method as in claim 12, further comprising:
collecting the first data with a sensor system that comprises a carbon dioxide analyzer that determines the measured carbon dioxide concentration and an oxygen analyzer that determines the measured oxygen concentration.

14. A system comprising:
one or more processors; and
at least one computer readable medium, the at least one computer readable medium storing instructions that, when executed by the one or more processors, cause the one or more processors to perform operations comprising:
receiving, at the one or more processors, first data representative of a first measured carbon dioxide ($CO_2$) concentration and of a first measured oxygen ($O_2$) concentration at a first measurement location;
determining, by the one or more processors using input data comprising the first data, that the measured carbon dioxide concentration at the first measurement location is elevated relative to a baseline carbon dioxide concentration due to escape of carbon dioxide from a source associated with a carbon capture and storage process, the determining comprising accounting for observed variability in the first measured carbon dioxide concentration expected to be attributable to one or more of respiration or photosynthesis of living organisms, combustion of fossil fuels, combustion of biofuels, or combustion of biomatter in a local vicinity of the first measurement site the accounting for comprising detecting a change in a termporal correlation between the first measured carbon dioxide concentration and the first measured oxygen concentration at the first measurement location; and
promoting a result indicating possible escape of carbon dioxide from the source.

15. A system comprising:
one or more processors; and
at least one computer readable medium, the at least one computer readable medium storing instructions that, when executed by the one or more processors, cause the one or more processors to perform operations comprising:
receiving, at the one or more processors, first data representative of a first measured carbon dioxide ($CO_2$) concentration and of a first measured oxygen ($O_2$) concentration at a first measurement location;
determining, by the one or more processors using input data comprising the first data, that the measured carbon dioxide concentration at the first measurement location is elevated relative to a baseline carbon dioxide concentration due to escape of carbon dioxide from a source associated with a carbon capture and storage process;
quantifying, based on the first data, a first carbon dioxide concentration increase at the first location that is attributable to escape of carbon dioxide from the source;
calculating a rate of escape of carbon dioxide from the source, the calculating comprising executing a model of gas-phase transport using at least the first carbon dioxide concentration increase; and
promoting a result indicating possible escape of carbon dioxide from the source.

16. A system comprising:
one or more processors; and
at least one computer readable medium, the at least one computer readable medium storing instructions that, when executed by the one or more processors, cause the one or more processors to perform operations comprising:
receiving, at the one or more processors, first data representative of a first measured carbon dioxide ($CO_2$) concentration and of a first measured oxygen ($O_2$) concentration at a first measurement location and second data representative of a second measured carbon dioxide concentration and of a second measured oxygen concentration at a second measurement location;
determining, by the processor using input data comprising the first data, that the measured carbon dioxide concentration at the first measurement location is elevated relative to a baseline carbon dioxide concentration due to escape of carbon dioxide from a source associated with a carbon capture and storage process;
isolating a source location for the source using at least the first data and the second data; and
promoting a result indicating possible escape of carbon dioxide from the source.

17. A system as in claim 16, further comprising:
a carbon dioxide analyzer that determines the measured carbon dioxide concentration;
an oxygen analyzer that determines the measured oxygen concentration;
a navigation system that determines the first measurement location and the second measurement location; and
a mobile chassis that houses the carbon dioxide analyzer, the oxygen analyzer, the navigation system, and the one or more processors; the operations further comprising collecting the first data and the second data using the carbon dioxide analyzer and the oxygen analyzer while the mobile chassis is positioned at the first measurement location and the second measurement location, respectively.

18. A computer-readable, non-transitory storage medium storing instructions that, when executed by one or more processors, cause the one or more processors to perform operations comprising comprising:
receiving, at the one or more processors, first data representative of a first measured carbon dioxide ($CO_2$) concentration and of a first measured oxygen ($O_2$) concentration at a first measurement location;
determining, by the one or more processors using input data comprising the first data, that the measured carbon dioxide concentration at the first measurement location is elevated relative to a baseline carbon dioxide concentration due to escape of carbon dioxide from a source associated with a carbon capture and storage process, the determining comprising accounting for observed variability in the first measured carbon dioxide concentration expected to be attributable to one or more of respiration or photosynthesis of living organisms, combustion of fossil fuels, combustion of biofuels, or combustion of biomatter in a local vicinity of the first measurement site, the accounting for comprising detecting a change in a temporal correlation between the first measured carbon dioxide concentration and the first measured oxygen concentration at the first measurement location; and
promoting a result indicating possible escape of carbon dioxide from the source.

19. A computer-readable, non-transitory storage medium storing instructions that, when executed by one or more processors, cause the one or more processors to perform operations comprising:

receiving, at the one or more processors, first data representative of a first measured carbon dioxide ($CO_2$) concentration and of a first measured oxygen ($O_2$) concentration at a first measurement location;

determining, by the one or more processors using input data comprising the first data, that the measured carbon dioxide concentration at the first measurement location is elevated relative to a baseline carbon dioxide concentration due to escape of carbon dioxide from a source associated with a carbon capture and storage process;

quantifying, based on the first data, a first carbon dioxide concentration increase at the first location that is attributable to escape of carbon dioxide from the source;

calculating a rate of escape of carbon dioxide from the source, the calculating comprising executing a model of gas-phase transport using at least the first carbon dioxide concentration increase; and promoting a result indicating possible escape of carbon dioxide from the source.

20. A computer-readable, non-transitory storage medium storing instructions that, when executed by one or more processors, cause the one or more processors to perform operations comprising:

receiving, at the one or more processors, first data representative of a first measured carbon dioxide ($CO_2$) concentration and of a first measured oxygen ($O_2$) concentration at a first measurement location and second data representative of a second measured carbon dioxide concentration and of a second measured oxygen concentration at a second measurement location;

determining, by the processor using input data comprising the first data, that the measured carbon dioxide concentration at the first measurement location is elevated relative to a baseline carbon dioxide concentration due to escape of carbon dioxide from a source associated with a carbon capture and storage process;

isolating a source location for the source using at least the first data and the second data; and promoting a result indicating possible escape of carbon dioxide from the source.

* * * * *